US008799087B2

(12) United States Patent
Martin et al.

(10) Patent No.: US 8,799,087 B2
(45) Date of Patent: Aug. 5, 2014

(54) SYSTEMS, METHODS, AND COMPUTER READABLE MEDIA FOR UTILIZING ONE OR MORE PREFERRED APPLICATION LISTS IN A WIRELESS DEVICE READER

(75) Inventors: Philippe Martin, San Jose, CA (US); Mohammad Khan, San Jose, CA (US); Jean-Christophe Raynon, San Jose, CA (US)

(73) Assignee: MasterCard International Incorporated, Purchase, NY (US)

(*) Notice: Subject to any disclaimer, the term of this patent is extended or adjusted under 35 U.S.C. 154(b) by 196 days.

(21) Appl. No.: 13/283,521

(22) Filed: Oct. 27, 2011

(65) Prior Publication Data
US 2012/0109764 A1 May 3, 2012

Related U.S. Application Data

(60) Provisional application No. 61/407,267, filed on Oct. 27, 2010.

(51) Int. Cl.
| | |
|---|---|
| *G06Q 20/00* | (2012.01) |
| *G06Q 40/00* | (2012.01) |
| *G06F 17/00* | (2006.01) |
| *G06K 15/00* | (2006.01) |
| *G06K 5/00* | (2006.01) |
| *G06Q 20/20* | (2012.01) |
| *G06Q 20/10* | (2012.01) |
| *G06F 7/08* | (2006.01) |
| *G06F 19/20* | (2011.01) |

(52) U.S. Cl.
CPC .............. *G06Q 20/20* (2013.01); *G06Q 20/204* (2013.01); *G06Q 20/10* (2013.01); *G06F 7/08* (2013.01); *G06F 19/20* (2013.01)
USPC ................... 705/17; 705/16; 705/39; 705/64; 705/67; 235/375; 235/379; 235/380; 235/381

(58) Field of Classification Search
CPC ..... G06Q 20/204; G06Q 20/20; G06Q 20/10; G06Q 20/382; G06Q 30/02; G06F 7/1008; G06F 7/08; G06F 19/20
USPC ............ 705/17, 39, 64, 16, 67; 235/380, 379, 235/381, 375; 455/41.2, 414.1, 405, 406, 455/407
See application file for complete search history.

(56) References Cited

U.S. PATENT DOCUMENTS 4,120,011 A 10/1978 Kolb, Jr.
4,575,621 A 3/1986 Dreifus
(Continued)

FOREIGN PATENT DOCUMENTS

EP 0 863 477 A1 9/1998
EP 0 949 593 A2 10/1999
(Continued)

OTHER PUBLICATIONS

Commonly-assigned, co-pending U.S. Appl. No. 13/584,553 for "Collaborative Negotiation Techniques for Mobile Personal Trusted Device Financial Transactions,"(Unpublished, filed Aug. 13, 2012).

(Continued)

*Primary Examiner* — Olusegun Goyea
(74) *Attorney, Agent, or Firm* — Jenkins, Wilson, Taylor & Hunt, P.A.

(57) ABSTRACT

The subject matter described herein includes systems, methods, and computer readable media for utilizing one or more preferred application lists in a wireless device reader. A transaction terminal designates compatible application identifiers, where each of the compatible application identifiers is respectively associated with a transaction application that is compatible with the transaction terminal. A proximity payment system environment (PPSE) application is configured to store user preferred application identifiers, where each user preferred application identifier is respectively associated with a to transaction application stored on the mobile wireless device. A wireless device reader for receives the compatible application identifiers from the transaction terminal, and stores the compatible application identifiers in preferred applications lists (PALs).

37 Claims, 3 Drawing Sheets

(56) References Cited

U.S. PATENT DOCUMENTS

| | | | |
|---|---|---|---|
| 4,701,601 A | 10/1987 | Francini et al. | |
| 4,758,714 A | 7/1988 | Carlson et al. | |
| 4,788,420 A | 11/1988 | Chang et al. | |
| 4,973,828 A | 11/1990 | Naruse et al. | |
| 5,157,247 A | 10/1992 | Takahira | |
| 5,266,789 A | 11/1993 | Anglin et al. | |
| 5,276,311 A | 1/1994 | Hennige | |
| 5,530,232 A | 6/1996 | Taylor | |
| 5,590,038 A | 12/1996 | Pitroda | |
| 5,594,233 A | 1/1997 | Kenneth et al. | |
| 5,602,377 A | 2/1997 | Beller et al. | |
| 5,608,193 A | 3/1997 | Almogaibil | |
| 5,679,945 A | 10/1997 | Renner et al. | |
| 5,781,723 A | 7/1998 | Yee et al. | |
| 5,796,828 A | 8/1998 | Tsukamoto et al. | |
| 5,797,470 A | 8/1998 | Bohnert et al. | |
| 5,850,077 A | 12/1998 | Tognazzini | |
| 5,859,419 A | 1/1999 | Wynn | |
| 5,878,141 A | 3/1999 | Daly et al. | |
| 5,917,168 A | 6/1999 | Nakamura et al. | |
| 5,955,961 A | 9/1999 | Wallerstein | |
| 5,991,410 A | 11/1999 | Albert et al. | |
| 6,018,717 A | 1/2000 | Lee et al. | |
| 6,038,491 A | 3/2000 | McGarry et al. | |
| 6,061,665 A | 5/2000 | Bahreman | |
| 6,068,183 A | 5/2000 | Freeman et al. | |
| 6,131,811 A | 10/2000 | Gangi | |
| 6,141,161 A | 10/2000 | Sato et al. | |
| 6,155,484 A | 12/2000 | Sasaki | |
| 6,175,922 B1 | 1/2001 | Wang | |
| 6,181,981 B1 | 1/2001 | Varga et al. | |
| 6,189,791 B1 | 2/2001 | Takita et al. | |
| 6,206,293 B1 | 3/2001 | Gutman et al. | |
| 6,233,448 B1 | 5/2001 | Alperovich et al. | |
| 6,250,557 B1 | 6/2001 | Forslund et al. | |
| 6,293,462 B1 | 9/2001 | Gangi | |
| 6,295,482 B1 | 9/2001 | Tognazzini | |
| 6,446,864 B1 | 9/2002 | Kim et al. | |
| 6,584,309 B1 | 6/2003 | Whigham | |
| 6,637,653 B1 | 10/2003 | Takita et al. | |
| 6,658,248 B1 | 12/2003 | Lee | |
| 6,662,224 B1 | 12/2003 | Angwin et al. | |
| 6,704,567 B1 | 3/2004 | Chapman, Jr. et al. | |
| 6,711,263 B1 | 3/2004 | Nordenstam et al. | |
| 6,769,607 B1 | 8/2004 | Pitroda et al. | |
| 6,808,111 B2 * | 10/2004 | Kashef et al. | 235/380 |
| 6,844,813 B2 | 1/2005 | Hardman | |
| 7,028,897 B2 | 4/2006 | Fernandes et al. | |
| 7,051,932 B2 | 5/2006 | Fernandes et al. | |
| 7,127,236 B2 | 10/2006 | Khan et al. | |
| 7,494,055 B2 | 2/2009 | Fernandes et al. | |
| 7,775,442 B2 | 8/2010 | Saarisalo | |
| 8,240,557 B2 | 8/2012 | Fernandes et al. | |
| 8,275,694 B2 | 9/2012 | Tzroya | |
| 8,523,053 B2 * | 9/2013 | Royyuru et al. | 235/379 |
| 8,596,528 B2 | 12/2013 | Fernandes et al. | |
| 2001/0034566 A1 | 10/2001 | Offer | |
| 2002/0062249 A1 | 5/2002 | Iannacci | |
| 2002/0128981 A1 | 9/2002 | Kawan et al. | |
| 2002/0175207 A1 * | 11/2002 | Kashef et al. | 235/380 |
| 2003/0055735 A1 | 3/2003 | Cameron et al. | |
| 2003/0169180 A1 | 9/2003 | Hardman | |
| 2003/0172028 A1 | 9/2003 | Abell et al. | |
| 2003/0229583 A1 | 12/2003 | Cotten et al. | |
| 2004/0068472 A1 * | 4/2004 | Sahota et al. | 705/64 |
| 2004/0159700 A1 | 8/2004 | Khan et al. | |
| 2004/0181453 A1 | 9/2004 | Ray et al. | |
| 2004/0249839 A1 * | 12/2004 | Beenau et al. | 707/100 |
| 2005/0004866 A1 * | 1/2005 | Bonalle et al. | 705/39 |
| 2005/0004921 A1 * | 1/2005 | Beenau et al. | 707/100 |
| 2005/0035192 A1 * | 2/2005 | Bonalle et al. | 235/379 |
| 2005/0059339 A1 | 3/2005 | Honda et al. | |
| 2005/0060062 A1 | 3/2005 | Walker et al. | |
| 2005/0128981 A1 | 6/2005 | Creamer et al. | |
| 2005/0171898 A1 * | 8/2005 | Bishop et al. | 705/39 |
| 2005/0192896 A1 | 9/2005 | Hutchinson et al. | |
| 2005/0222961 A1 * | 10/2005 | Staib et al. | 705/64 |
| 2006/0000900 A1 | 1/2006 | Fernandes et al. | |
| 2006/0002610 A1 | 1/2006 | Suomela et al. | |
| 2007/0192245 A1 | 8/2007 | Fisher | |
| 2008/0147508 A1 * | 6/2008 | Liu et al. | 705/17 |
| 2008/0167000 A1 * | 7/2008 | Wentker et al. | 455/408 |
| 2008/0167017 A1 * | 7/2008 | Wentker et al. | 455/414.1 |
| 2008/0207128 A1 * | 8/2008 | Mikko | 455/41.2 |
| 2008/0306849 A1 * | 12/2008 | Johnson et al. | 705/35 |
| 2009/0108064 A1 | 4/2009 | Fernandes et al. | |
| 2010/0051685 A1 * | 3/2010 | Royyuru et al. | 235/379 |
| 2010/0160714 A1 | 6/2010 | Chua et al. | |
| 2010/0325052 A1 * | 12/2010 | Sahota et al. | 705/67 |
| 2011/0244796 A1 | 10/2011 | Khan et al. | |
| 2012/0011070 A1 * | 1/2012 | Ward et al. | 705/72 |
| 2012/0109764 A1 * | 5/2012 | Martin et al. | 705/17 |
| 2013/0015241 A1 | 1/2013 | Fernandes et al. | |
| 2013/0080273 A1 * | 3/2013 | Royyuru | 705/16 |

FOREIGN PATENT DOCUMENTS

| | | |
|---|---|---|
| EP | 1 104 909 A2 | 6/2001 |
| KR | 10-2007-0073718 | 7/2007 |
| KR | 10-2009-0029323 | 3/2009 |
| WO | WO 01/37199 A1 | 5/2001 |
| WO | WO 01/37200 A1 | 5/2001 |
| WO | WO 03/058947 A2 | 7/2003 |
| WO | WO 2011/127084 A2 | 10/2011 |

OTHER PUBLICATIONS

Non-Final Official Action for U.S. Appl. No. 13/080,613 (Aug. 6, 2012).

Notice of Allowance and Fee(s) Due for U.S. Appl. No. 12/287,283 (Apr. 16, 2012).

Non-Final Official Action for U.S. Appl. No. 13/080,613 (Apr. 5, 2012).

Final Official Action for U.S. Appl. No. 10/428,502 (Feb. 8, 2012).

Notice of Allowance and Fee(s) Due for U.S. Appl. No. 12/287,283 (Jan. 10, 2012).

Notice of Allowance and Fee(s) Due for U.S. Appl. No. 12/287,283 (Nov. 23, 2011).

Notification of Transmittal of the International Search Report and the Written Opinion of the International Searching Authority, or the Declaration for International Application No. PCT/US2011/031293 (Oct. 24, 2011).

Non-Final Official Action for U.S. Appl. No. 12/287,283 (Mar. 1, 2011).

Non-Final Official Action for U.S. Appl. No. 10/428,502 (Jul. 19, 2010).

Decision on Appeal for U.S. Appl. No. 10/428,502 (Feb. 23, 2010).

Reply Brief Noted for U.S. Appl. No. 10/428,502 (Dec. 3, 2008).

Examiner's Answer for U.S. Appl. No. 10/428,502 (Aug. 25, 2008).

Notice of Allowance and Fee(s) Due for U.S. Appl. No. 11/137,682 (Jun. 30, 2008).

"Part III: Files, Commands, and Application Selection," EMV Integrated Circuit Card Specifications for Payment Systems, Book 1: Application Independent ICC to Terminal Interface Requirements, Version 4.2, pp. 119-150 (Jun. 2008).

"10. Data Management," EMV Integrated Circuit Card Specifications for Payment Systems, Book 4: Cardholder, Attendent, and Acquirer Interface Requirements, Version 4.2, pp. 81-94 (Jun. 2008).

Notice of Panel Decision from Pre-Appeal Brief Review for U.S. Appl. No. 10/428,502 (May 14, 2008).

Notice of Panel Decision from Pre-Appeal Brief Review for U.S. Appl. No. 11/137,682 (Apr. 25, 2008).

Final Official Action for U.S. Appl. No. 11/137,682 (Dec. 13, 2007).

Final Official Action for U.S. Appl. No. 10/428,502 (Nov. 28, 2007).

Non-Final Official Action for U.S. Appl. No. 10/428,502 (Apr. 16, 2007).

Non-Final Official Action for U.S. Appl. No. 11/137,682 (Mar. 20, 2007).

Final Official Action for U.S. Appl. No. 10/428,502 (Aug. 15, 2006).

Non-Final Official Action for U.S. Appl. No. 10/428,502 (Dec. 22, 2005).

(56) References Cited

OTHER PUBLICATIONS

"Identification cards—Integrated circuit cards—Part 4: Organization, security and commands for interchange," ISO/IEC 7816-4, Second Edition, pp. 1-90 (Jan. 15, 2005).

"Information technology—Telecommunications and information exchange between systems—Near Field Communications—Interface and Protocol (NFCIP-1)," ISO/IEC 18092, pp. 1-66 (Apr. 1, 2004).

"Identification cards—Contactless integrated circuit(s) cards—Proximity cards—Part 2: Radio frequency power and signal interface," ISO/IEC 14443-2, pp. 1-10 (Jul. 22, 2003).

Commonly-assigned, co-pending U.S. Appl. No. 10/428,502 for "Collaborative Negotiation Techniques for Mobile Personal Trusted Device Financial Transactions," (Unpublished, filed May 2, 2003).

"Information technology—Identification cards—Integrated circuit(s) cards with contacts—Part 5: Registration of application providers," ISO/IEC 7816-5.2, pp. 1-12 (Jan. 17, 2003).

"Information technology—Identification cards—Integrated circuit(s) cards with contacts—Part 4: Interindustry commands for interchange," ISO/IEC 7816-4, pp. 1-85 (Jan. 17, 2003).

"Identification cards—Contactless integrated circuit(s) cards—Vicinity cards—Part 3: Anticollision and transmission protocol," ISO/IEC 15693-3, First Edition, pp. 1-50 (Apr. 1, 2001).

"Identification cards—Recording technique—Part 2: Magnetic stripe—Low coercivity," ISO/IEC 7811-2, Third Edition, pp. 1-28 (Feb. 1, 2001).

"Identification cards—Contactless integrated circuit(s) cards—Vicinity cards—Part 1: Physical characteristics," ISO/IEC 15693-1, First Edition, pp. 1-12 (Jul. 15, 2000).

"Identification cards—Contactless integrated circuit(s) cards—Vicinity cards—Part 2: Air interface and intialization," ISO/IEC 15693-2, First Edition, pp. 1-19 (May 1, 2000).

"Identification cards—Contactless integrated circuit(s) cards—Proximity cards—Part 4: Transmission protocol," ISO/IEC 14443-4, pp. 1-39 (Mar. 10, 2000).

Petri, "An Introduction to Smart Cards," Litronic, Inc., Messaging Magazine, pp. 1-12 (Sep./Oct. 1999).

"Identification cards—Contactless integrated circuit(s) cards—Proximity cards—Part 3: Intialization and anticollision," ISO/IEC 14443-3, pp. 1-48 (Jun. 11, 1999).

"Identification cards—Integrated circuit(s) cards with contacts—Part 5: Numbering system and registration procedure for application identifiers," ISO/IEC 7816-5, Amendment 1, pp. 1-8 (Dec. 15, 1996).

"Identification cards—Integrated circuit(s) cards with contacts—Part 5: Numbering system and registration procedure for application identifiers," ISO/IEC 7816-5, First Edition, pp. 1-12 (Jun. 15, 1994).

Notice of Allowance and Fee(s) Due for U.S. Appl. No. 13/584,553 (Aug. 6, 2013).

Final Office Action for U.S. Appl. No. 13/080,613 (Jan. 17, 2013).

Communication of European publication number and information on the application of Article 67(3) EPC for Application No. 11766608.1 (Jan. 16, 2013).

Non-Final Office Action for U.S. Appl. No. 13/584,553 (Jan. 15, 2013).

\* cited by examiner

SYSTEMS, METHODS, AND COMPUTER READABLE MEDIA FOR UTILIZING ONE OR MORE PREFERRED APPLICATION LISTS IN A WIRELESS DEVICE READER

PRIORITY CLAIM

This application claims the benefit of U.S. Provisional Patent Application Ser. No. 61/407,267 filed on Oct. 27, 2010, the disclosure of which is incorporated herein by reference, in its entirety.

TECHNICAL FIELD

The subject matter described herein relates to conducting wireless payment and non-payment transactions with a mobile wireless device via near field communication (NFC). More particularly, the subject matter described herein relates to systems, methods, and computer readable media for utilizing one or more preferred application lists in a wireless device reader.

BACKGROUND

Currently, various transactions in purchasing environments can be performed using wireless smart devices, for example near field communication (NFC) devices. Such transactions can include, without limitation, ordering goods and/or services, paying for goods and/or services, specifying personal preferences or personal data relating to goods and/or services, returning previously purchased goods and/or services, and redeeming coupons, customer loyalty points, promotions and/or combinations thereof. In addition, wireless transactions involving NFC devices typically require at least a two-step approach with a separate tap for each transaction. For example, the first step can include tapping the NFC device to the NFC wireless device reader to communicate value added applications including, for example, the order and/or coupon transactions. The second step can include tapping the NFC device to the NFC wireless reader for communicating the payment transaction. That is, more than one NFC tap is necessary to convey information for the order, coupon, and payment transactions in the sandwich example. This can be both cumbersome and time-consuming.

NFC enabled mobile wireless devices and contactless smart cards, as per the EMV specifications, may be provisioned with a Proximity Payment System Environment (PPSE) application. The PPSE application may be configured to provide a wireless device reader with a list of transaction application identifiers that corresponds to a plurality of transaction applications stored in the wireless device. Notably, these transaction applications have been designated by the user as appropriate to use for a wireless payment or non-payment transaction. Also, each of the application identifiers listed in the PPSE application also include a priority level such that the application identifiers may be prioritized in an order that represents the user's transaction application preference to attempt to conduct the wireless transaction. Upon initiation of the wireless transaction, the reader is typically required to select the highest priority application the reader is configured to support. This arrangement, however, may not be feasible with respect to a merchant entity's business model that would be better served if the merchant possessed the ability to control the priorities of the selection process of payment and/or non-payment transaction applications and data.

Accordingly, there exists a need for methods and systems that utilize one or more preferred application lists in a wireless device reader.

SUMMARY

According to one aspect, the subject matter described herein includes a system for utilizing one or more preferred application lists in a NFC reader. The system includes a transaction terminal for designating a plurality of compatible application identifiers, wherein each of the compatible application identifiers is respectively associated with a transaction application that is compatible with the transaction terminal. The system also includes a mobile wireless device provisioned with a proximity payment system environment (PPSE) application that is configured to store a plurality of user preferred application identifiers, wherein each user preferred application identifier is respectively associated with a transaction application stored on the mobile wireless device. The system further includes a wireless device reader for receiving the plurality of compatible application identifiers from the transaction terminal, for storing the compatible application identifiers among a plurality of preferred applications lists (PALs) which includes a first PAL configured to store a first group of the compatible application identifiers, wherein each of the compatible application identifiers in the first group is assigned a priority indicator, for receiving a PPSE list containing the user preferred application identifiers from the PPSE application in response to an initiation of a wireless transaction by the mobile wireless device, for determining one or more matched application identifiers by comparing each of the compatible application identifiers contained in the first PAL with each of the user preferred application identifiers, for identifying a single matched application identifier from the one or more matched application identifiers, wherein the single matched application identifier matches the compatible application identifier with the highest priority indicator stored in the first PAL, and for requesting transaction application data from the transaction application associated with the single matched application identifier.

As used herein, the term "mobile wireless device" refers to a wireless device or wireless smart device that can communicate via an electric and/or magnetic field between the device and some other entity, usually a wireless terminal or wireless smart device reader. One type of wireless device that can wirelessly communicate to a wireless smart device reader is an NFC card or NFC handheld device, including but not limited to a smart phone. In near field communication, a wireless smart device may communicate with a wireless smart device reader via inductive coupling of the reader antenna to the device antenna. The two loop antennas effectively form a transformer. The reader amplitude-modulates the radio frequency (RF) field to send information to the device. The device communicates with the reader by modulating the loading on the device antenna, which also modulates the load on the reader antenna. In a wireless smart device, the NFC handset enables contactless payment, and a security element (SE) for ensuring secure transactions can be embedded, provided by a universal subscriber identity module (USIM), or provided as an add-on to, for example, a SD or a jacket.

Wireless smart devices can communicate with a wireless device reader using NFC. As used herein, the term "wireless communications" includes communications conducted at ISO 14443 and ISO 18092 interfaces. Namely, wireless communications over an NFC link may be established using a card emulation mode (e.g., in accordance with ISO 14443) or a peer to peer mode (e.g. in accordance with ISO 18092) of communication. These specifications define communication protocols for wireless smart devices operating in close proximity with a reader antenna. In one embodiment, wireless communications can communicate applications that are uniquely identified by an application identifier (AID), defined by the ISO/IEC 7816 specification. Application to terminal interface requirements are also defined in book 4 of the Europay MasterCard Visa (EMV) 4.2 specification.

The subject matter described herein may be implemented in software, in combination with hardware and/or firmware. For example, the subject matter described herein may be implemented in software executed by a processor. In one exemplary implementation, the subject matter described herein for utilizing one or more preferred application lists in a NFC reader may be implemented using a non-transitory computer readable medium to having stored thereon executable instructions that when executed by the processor of a computer control the processor to perform steps. Exemplary non-transitory computer readable media suitable for implementing the subject matter described herein include chip memory devices or disk memory devices accessible by a processor, programmable logic devices, and application specific integrated circuits. In addition, a computer readable medium that implements the subject matter described herein may be located on a single computing platform or may be distributed across plural computing platforms.

BRIEF DESCRIPTION OF THE DRAWINGS

Preferred embodiments of the subject matter described herein will now be explained with reference to the accompanying drawings, wherein like reference numerals represent like parts, of which.

DETAILED DESCRIPTION

Figure 1:
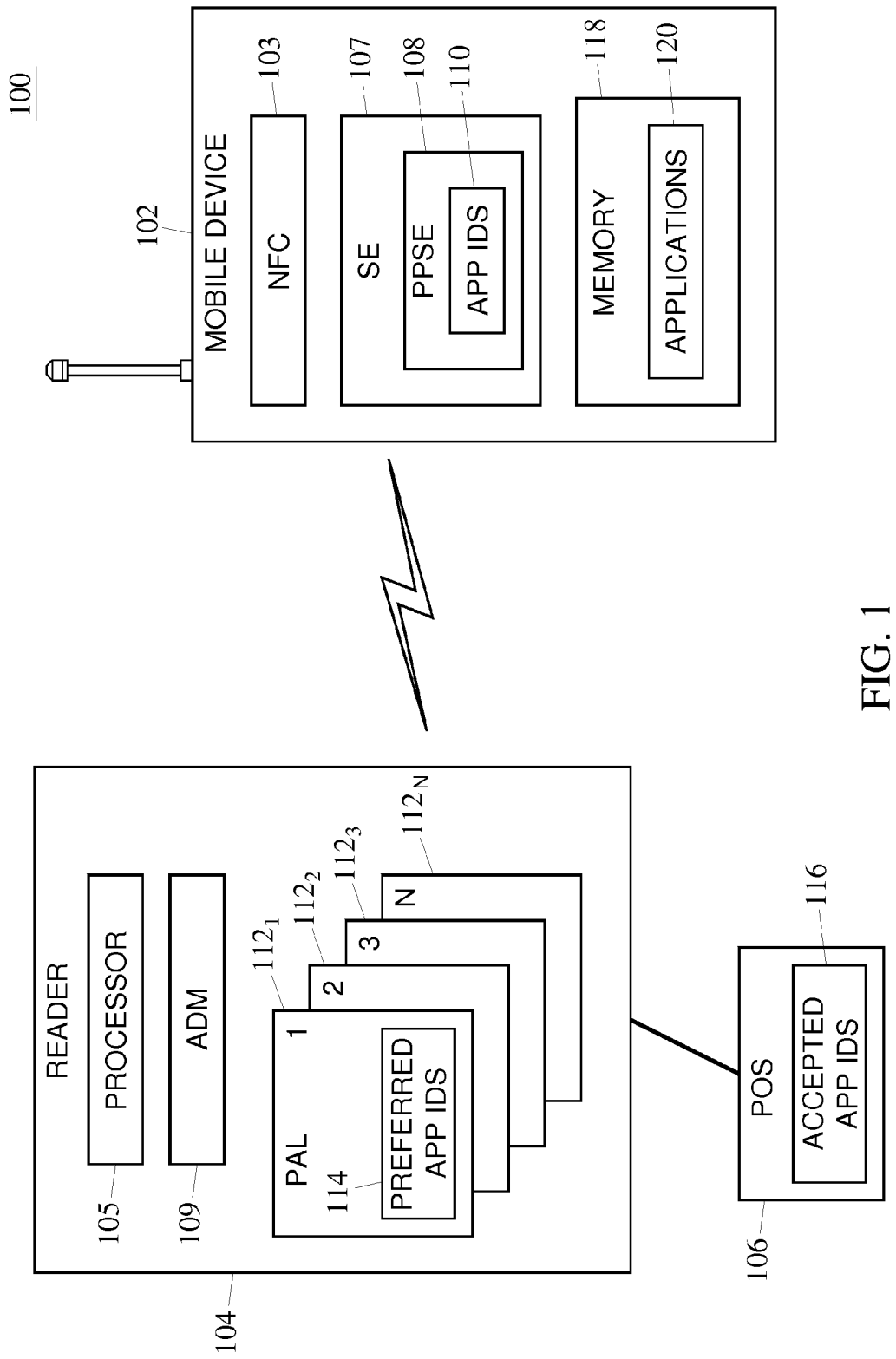
FIG. 1 is a block diagram illustrating an exemplary system for utilizing one or more preferred application lists in a NFC reader according to an embodiment of the subject matter described herein.

In accordance with the subject matter disclosed herein, systems, methods, and computer readable media are provided for utilizing one or more preferred application lists (PALs) in a wireless device reader. Referring to FIG. 1, a system 100 generally designated for utilizing one or more preferred application lists in a wireless device reader (e.g., a near field communication (NFC) reader) to facilitate a wireless transaction is illustrated. System 100 may include a mobile wireless device 102, a wireless device reader 104, and a transaction terminal 106, such as a point of sale (POS) terminal. Wireless device 102 and wireless device reader 104 may interface and communicate via respective loop antennas (not shown) activated by one or more contactless NFC taps of the device in proximity to the reader. In one embodiment, wireless device 102 may include at least one secure element 107 for storing a proximity payment system environment (PPSE) application 108. PPSE application 108 may include an application for maintaining a priority listing of transaction application identifiers that correspond to transaction applications 120 hosted or stored on wireless device 102. In one embodiment, secure element 107 includes a secure element (SE) memory, where PPSE application 108 may be accessed during a secure and authenticated session.

In one embodiment, one or more application identifiers (AIDs) can be stored in PPSE application 108 residing in secure element 107, which may include a hardware based SE chipset, a SE memory, and a SE memory portion that links to a baseband memory. PPSE application 108, however, does not require authentication and/or secure sessions to be used. In one embodiment, PPSE 108 may reside in a non-secure baseband memory 118 of wireless device 102 or in a non-secure hardware element (not shown).

In one embodiment, transaction terminal 106 may be used to define a list of application identifiers (i.e., "App IDs" or "AIDs") that identify transaction applications a merchant entity prefers and is willing to accept in a wireless transaction (i.e., applications that are compatible with terminal 106 and/or reader 104). Although the following description details a purchase transaction, non-payment transaction may be conducted in a similar manner without departing from the scope of the present subject matter. Non-payment transactions may include, without limitation, applications for loyalty cards, loyalty points, coupons, ordering information, promotions, personal preferences, personalized data, product return information and/or any other suitable application or combinations thereof used to conduct a non-payment transaction at transaction terminal 106.

Once provisioned with the list of compatible AIDs, transaction terminal 106 may communicate the list information to wireless smart device reader 104. The compatible AIDs data is then populated into separate categorical lists that are local to reader 104 called Preferred Application Lists (PALs). Once assigned and grouped to a PAL based on type, the compatible AIDs are assigned priority level indicators and become preferred application identifiers. The priority level indicator indicates the transaction application preferences a merchant entity wishes to conduct a wireless transaction. In one embodiment, a merchant entity may designate the priority level indicators using transaction terminal 106. Wireless device reader 104 may be able to support one or more PALs, e.g., PALs $112_{1...N}$, wherein each PAL is configured to store different types of application data in respective priority orders. For example, a PAL-1 may be configured to hold a priority listing of AIDs that identify a respective plurality of accepted electronic payment card applications that are compatible for processing by terminal 106 and/or reader 104. Similarly, a PAL-2 may be configured to hold one or more AIDs that identify a respective plurality of accepted electronic loyalty card applications and a PAL-3 may be configured to hold a priority listing of AIDs that identify a respective plurality of accepted electronic coupon applications. In one embodiment, PAL-2 may be configured to simply hold a single AID corresponding to a loyalty card application associated with the location of reader 104 (e.g., a Kroger loyalty card AID held in PAL-2 of a reader located at a Kroger store location). Device reader 104 may also be configured with additional PALs (e.g., PAL-N) to hold a priority listing of AIDS that identify other accepted transaction applications (e.g., transit cards, healthcare cards, etc.).

In one embodiment, wireless device 102 may include an NFC enabled handset device such as an NFC enabled mobile wireless device (e.g., an NFC enabled smart phone), NFC enabled tablet, a wireless smart card, or any other device that is equipped with an NFC module 103 or chipset that enables wireless device 102 to conduct NFC or wireless communications with other NFC enabled devices (e.g., wireless device reader 104). Wireless device 102 may also be provisioned with a PPSE 108 for storing transaction application identifiers corresponding to transaction applications. Notably, PPSE application 108 includes multiple stored application identifiers (AIDs) 110 that respectively identify and correspond to applications 120 stored in memory 118. Transaction application identifiers may also be stored in other areas local to wireless device 102, such as in memory 118, in an applet (not shown) or some other location separate from the PPSE application 108 that is also accessible by wireless device reader 104. In one embodiment, AIDs 110 may identify and correspond to a payment or non-payment applications 120 located on device 102. Application data associated with applications 120 may be accessed and processed by AIDs selection module 109 to complete a wireless (payment or non-payment) transaction. Such transactions may include, but are not limited to, ordering goods and/or services, paying for goods and/or services, specifying personal preferences or personal data relating to goods and/or services, returning previously purchased goods and/or services, and redeeming coupons, customer loyalty points, promotions and/or combinations thereof.

Still referring to FIG. 1, wireless device 102 may include a plurality of stored AIDs 110. In one embodiment, a plurality of AIDs may be populated within PPSE application 108 based upon user selection via a GUI or by device selection using a wallet client application (not shown) in the wireless device 102. In one embodiment, the wallet client application may comprise a software application (which may be executed by a processing unit in a mobile wireless device) that manages multiple electronic-based softcards (i.e., transaction applications) stored on the mobile wireless device. Electronic-based softcards or transaction applications may include electronic credit cards, debit cards, prepaid cards, electronic coupons, electronic tickets, gift cards, loyalty cards, transit cards, healthcare cards, and the like. Using the location information, the wallet client may then populate PPSE application 108 with AIDs associated with the location information. For example, an electronic Macy's credit card, an electronic Macy's loyalty card, and applicable electronic coupon may be provisioned in PPSE application 108 when the received location data indicates a Macy's store location. In one embodiment, an AID associated with a location may be triggered by a WiFi signal, a GPS signal, or a triangulation signal that is transmitted by the merchant entity and is received by wireless device 102 upon entering the store location or being within proximity of a certain distance of the entrance of the store. Specifically, stored AIDs 110 may be selected by a user and/or wireless device 102 using location data from a GPS module (not shown) disposed on the phone or using triangulation methods, such as GPS or WiFi triangulation. In another embodiment, stored AIDs 110 may be pre-programmed using firmware to be automatically populated within PPSE application 108, and may be stored in order of priority. In one embodiment, the plurality of AIDs 110 can be stored in a list format or directory format within PPSE application 108 and be made accessible by reader 104.

In one embodiment, stored AIDs 110 and preferred AIDs 116 may include a 16 byte data structure defined according to ISO/IEC 7816-4. The first five bytes of a given AID correspond to a registered identifier (RID) which uniquely identifies a specific payment or non-payment application provider. For example, the first five bytes can identify a payment application provided by VISA®, MasterCard®, American Express®, or any other suitable payment or non-payment merchant provider application, for example, a ViVOtech® application. An optional field within a given AID can be assigned by the application provider, or registrant, and can include up to the remaining 11 bytes of information. The information can include object or transaction data used in processing the payment or non-payment transaction application. This field is known as a Proprietary Application Identifier Extension (PIX) and may contain any 0-11 byte value specified by the provider. The PIX portion can typically define object data for one application to be processed at reader 104. The meaning of this field is defined only for the specific RID and need not be unique across different RIDs. In one embodiment, the RID and PIX portions of AIDs 110 and/or 116 are accessed by wireless device reader 104 upon interfacing wireless device 102 with reader 104. One or more AIDs 118 may be communicated in an order of pre-specified priority where wireless device reader 104. Multiple AIDs 110 residing in PPSE application 108 may be wirelessly accessed upon processing PPSE application 108 at wireless device reader 104 through the single NFC tap.

FIG. 1 further illustrates a PPSE application 108 disposed in a secure element 107 of wireless device 102. Although PPSE application 108 is shown to reside in secure element 107, PPSE application 108 may be stored in a non-secure element 103 or baseband memory 118 without departing from the scope of the present subject matter. PPSE application 108 can be accessed and processed by wireless device reader 104 when wireless device reader 104 is interfaced (e.g., an NFC tap) by mobile wireless device 102. One or more AIDs can be populated and stored in PPSE application 108. In one embodiment, AIDs 110 may become populated within PPSE application 108 using a wallet client application (not shown) or firmware residing on wireless device 102 which inputs an AID into PPSE application 108 corresponding to an application selected by user of wireless device 102. As noted earlier, AIDs 110 may identify applications to be used for payment and/or non-payment transactions optionally performed in a merchant or retail environment.

In one embodiment, wireless device reader 104 may include any reader capable of reading any wireless device attempting to conduct a wireless transaction, such as a wireless smart card, an NFC enabled mobile wireless device, a contactless payment type device, and the like. In one embodiment, wireless device reader 104 includes an AIDs determination module (ADM) 109 that may be used to determine, identify, and select one or more AIDs used to conduct a wireless transaction. ADM 109 may also be configured to process the transaction applications corresponding to the identified AIDs. In one embodiment, ADM 109 may include a hardware based processing unit or processor chip. In another embodiment, ADM 109 may include software or firmware that is executed by processing unit 105. Wireless device reader 104 may also be configured to wirelessly or otherwise with transaction terminal 106. Wireless device reader 104 may communicate payment data, non-payment data, transaction, and/or payload data to transaction terminal 106 upon processing one or more applications identified using one or more AIDs.

In one embodiment, wireless device reader 104 includes a plurality of PALs 112 that is populated with compatible/accepted AIDS 116 from transaction terminal 106. Upon receipt, AIDS 116 are distributed among the different PALs 112 based on the type of transaction application the AID identifies. For example, PAL-1 may be designated to store AIDs corresponding to electronic payment card applications (i.e., softcards), PAL-2 may be designated to store AIDs corresponding to loyalty card applications, and PAL-3 may be designated to store AIDs corresponding to electronic coupon applications. Once the compatible AIDs are placed in a PAL, the AID may be ranked and/or assigned a priority level indicator that represents the preference order in which the associated transaction application should be used for a wireless transaction. Once assigned a priority level indicator, the AID is referred to as a preferred AID.

After each PAL 112 is populated with preferred AIDs 114 received from POS terminal 106, reader 104 may be NFC tapped by wireless device 102 for the purpose of conducting a wireless transaction, such as a wireless purchase transaction. After mobile wireless device 102 interfaces (e.g., NFC taps) with reader 104, reader 104 accesses PPSE application 108 in order to access the stored AIDs 110. In one embodiment, reader 104 wirelessly sends a SELECT command to mobile wireless device 102. Although the SELECT command is associated with the ANSI standard, commands used to request information that are related to other protocols or standards may be without departing from the scope of the present subject matter. In response to receiving the SELECT command, wireless device 102 provides a listing of AIDs 110 to reader 104.

Upon receipt of the listing of user preferred AIDs 110 at wireless device reader 104, reader 104 may be configured to cross reference the listing of AIDs 110 with preferred application identifiers stored in PAL-1 $112_1$. In one embodiment, ADM 109 compares the digits of a received user preferred AID with the digits of a preferred PAL-1 AID 114. If there is a partial (e.g., first 5 digits) or an exact (e.g., all 16 digits) match, then ADM 109 may designate the matched AID as a candidate AID, which may or may not ultimately be selected to conduct the wireless transaction. For example, reader 104 may cross-reference or compare each of the received user preferred applications identifiers to find a matching preferred application identifier in PAL-1. If a single matching application identifier is found, then that application identifier will be used to request transaction application data from mobile device 102. If a plurality of matching payment application identifiers is found, then reader 104 inspects the application identifiers that matched and identifies which application identifier (from the matching payment application identifiers) is associated with the highest priority indicator (as specified by the preferred application identifiers in PAL-1).

As mentioned above, ADM 109 may also be configured to support selection of partial AIDs. Namely, if the AID present in PAL-1 matches the first bytes of an AID in the PPSE list but has a smaller length, the PAL-1 AID's priority is still applied. The minimum length of an AID resident in the PAL is its registered application provider Identifier (RID) which are the first five bytes of an AID (see ISO-7816-4). The maximum length of an AID resident in the PAL is 16 bytes (ref ISO7816-4). An example of how partial selection is performed by ADM 109 may be described as follows. Suppose the PAL-1 AID is A000000299 and the PPSE list AID is A000000299001001. Notably, the PAL AID (actually the RID in this example) only matches the first 5 bytes of the PPSE AID. As a result, ADM 109 would register this as two matching AIDs (i.e., the priority modification process occurs).

In one embodiment, reader 104 may then send a SELECT command containing the application identifier associated with the highest priority indicator to mobile wireless device in order to request the transaction application identified by the application identifier. In response to the SELECT command, wireless device 102 may then provide the application data (e.g., a credit card number) associated with the transaction application. If the remaining PALs (e.g., PAL-2, PAL-3, PAL-N, etc.) in reader 104 do not contain any AIDs, then the application data is placed into a payload and sent to transaction terminal 106 for processing. If at least one of the remaining PALs does contain an AID, such as PAL-2, then reader 104 may obtain the AID in PAL-2 and issue a SELECT command containing the AID. In response to the SELECT command, wireless device 102 may then determine if the received AID corresponds with any transaction application 120 stored on mobile device 102. If the transaction application is located, then the corresponding application data (e.g., a loyalty card number) associated with the transaction application is provided back to reader 104. At this time, if the remaining PALs in reader 104 do not contain any AIDs, then the application data from PAL-1 and PAL-2 are bundled together and placed into a payload to be sent transaction terminal 106 for processing. If at least one of the remaining PALs does contain an AID, then reader 104 may obtain the AID in the PAL and issue a SELECT command containing the AID in the same manner described above with respect to PAL-2.

Figure 2:
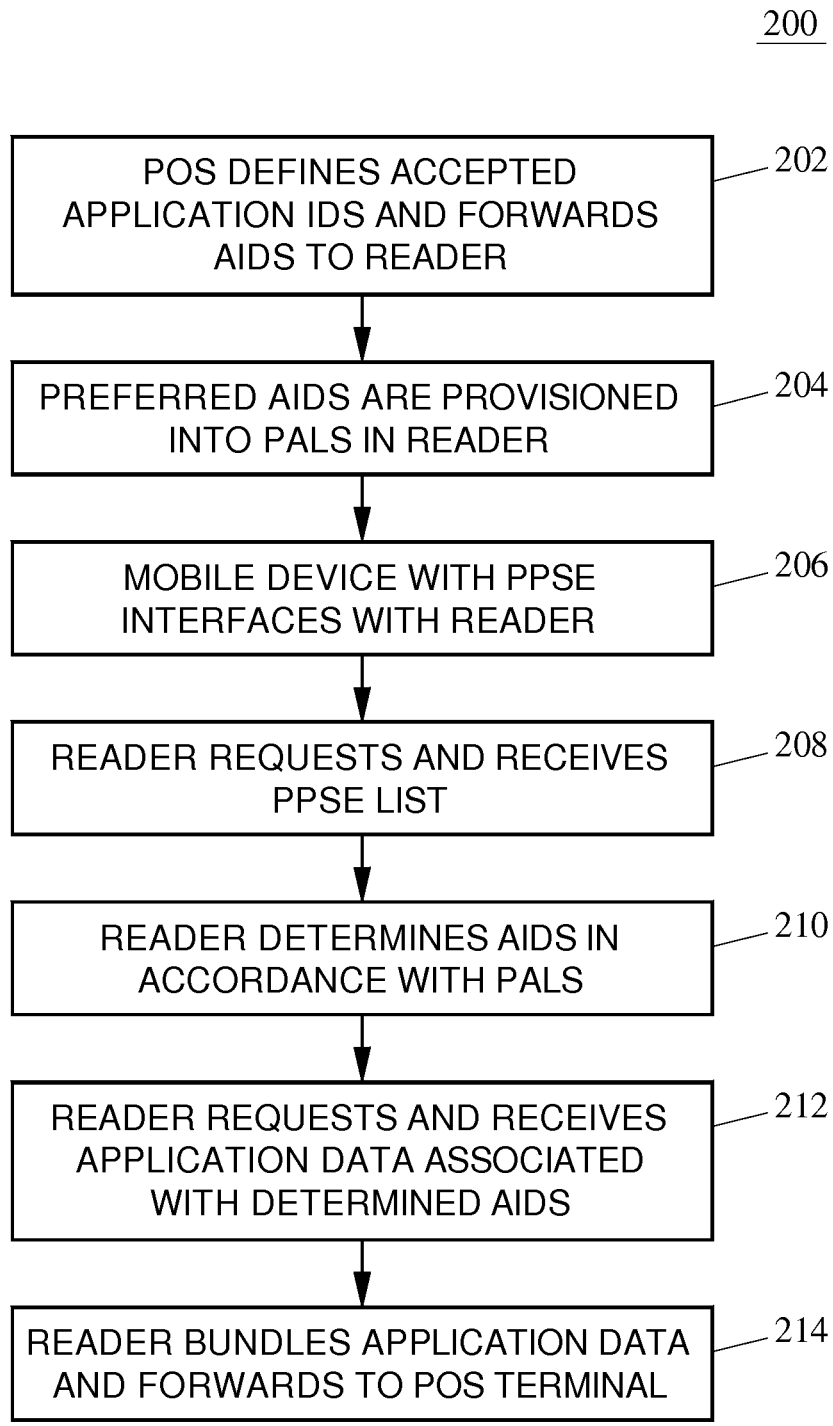
FIG. 2 is a flow chart illustrating an exemplary process for utilizing one or more preferred application lists in a NFC reader according to an embodiment of the subject matter described herein.

FIG. 2 is a flow chart illustrating an exemplary process for utilizing one or more preferred application lists in an NFC reader. In block 202, a plurality of accepted AIDs is defined. In one embodiment, POS terminal 106 is used to designate a plurality of AIDs 116 that are compatible with and may be accepted by reader 104 and used to conduct a wireless transaction, such as a payment transaction at point of sale (POS) terminal 106. The designated AIDs may be provided individually or collectively to reader 104.

In block 204, the accepted (i.e., compatible) AIDs are provisioned into PALs in the reader. In one embodiment, the compatible AIDs are categorized and stored in different PALs as preferred AIDs 114 depending on the type of transaction applications the AIDs identify. For example, PAL-1 $112_1$ may be the designated PAL for storing a list of preferred AIDs associated with compatible payment card applications, PAL-2 $112_2$ may be the designated PAL for storing one or more preferred AIDs associated with compatible loyalty card applications, and PAL-3 $112_3$ may be the designated PAL for storing a list of preferred AIDs associated with compatible electronic coupon applications. Thus, payment card AIDs may be placed in PAL-1, loyalty card AIDs may be placed in PAL-2, and electronic coupon AIDs may be placed in PAL-3. In other embodiments, other categorical types of AIDs (e.g., transit card AIDs) may be placed in a PAL-N.

In block 206, the mobile wireless device interfaces with wireless device reader. In one embodiment, mobile wireless device 102 provisioned with a PPSE initiates a wireless transaction by NFC tapping reader 104.

In block 208, the wireless device reader requests and receives a PPSE list. In one embodiment, reader 104 sends a SELECT PPSE command, which serves as a request message for the PPSE list. In response, reader 104 ultimately receives the PPSE listing containing the stored AIDS. In one embodiment, the PPSE listing may be embodied as a listing of user preferred AIDs and/or as FCI data.

In block 210, reader 104 determines the AIDS to be selected based on the specific PAL. In one embodiment, ADM 109 may be executed to compare the preferred AIDs present in PAL-1 with the user preferred AIDs contained in the PPSE listing. If only one match of AIDs is found, then that single matched AID will be used to request application data from the transaction application stored on the wireless device. If more than one matching is found, then ADM 109 may refer to the priority indicators associated with the preferred AIDs stored in PAL-1 and then select the AID with the highest priority indicator (e.g., priority 1 being the highest priority indicator, and priority 2 being higher than priority 3). One example as to how the preferred AIDs in PAL-1 are compared with the user preferred AIDs received from the wireless device may be described as follows. In one example, the PPSE list includes the following AIDs and respective priorities:
PPSE List content:
AID 1, PRIORITY_1
AID 2, PRIORITY_2
AID 3, PRIORITY_3
The PAL-1 contains the following AID and its respective priority:
PAL-1 content:
AID 2, PRIORITY_1
After comparing and processing the two sets of AIDs, ADM 109 may generate the resulting AID list for the decision process:
AID 2, PRIORITY_1
AID 1, PRIORITY_2
AID 3, PRIORITY_3
Consequently, ADM 109 identifies AID_2 as the matched AID with the highest priority (with regard to the priorities of the preferred AIDs) and may subsequently send a SELECT command including AID_2 to request application data from the transaction application in the wireless device identified by AID_2.

In a second example, the PPSE list includes the following AIDs and respective priorities:
PPSE content:
AID 1, PRIORITY_1
AID 2, PRIORITY_2
AID 3, PRIORITY_3
The PAL-1 contains the following AID and its respective priority:
PAL-1 content:
AID 2, PRIORITY_1
AID 3, PRIORITY_2
After comparing and processing the two sets of AIDs, ADM 109 may generate the resulting AID list for the decision process:
AID 2, PRIORITY_1
AID 3, PRIORITY_2
AID 1, PRIORITY_3
Consequently, ADM 109 identifies AID_2 as the matched AID with the highest priority (with regard to the priorities of the preferred AIDs) and may subsequently send a SELECT command including AID_2 to request application data from the transaction application in the wireless device identified by AID_2.

Returning to FIG. 2, in block 212, the wireless device reader requests and receives transaction application data associated with the determined AIDs. In one embodiment, reader 104 requests transaction application data from the transaction application associated with the single matched application identifier, i.e., the identified AID. For example, reader 104 may send a SELECT command that includes the identified matched AID to mobile wireless device 102. In response, mobile wireless device 102 determines that the matched AID identifies a transaction application 120. Wireless device 102 may then send application data associated with the identified transaction application back to reader 104. After receiving the application data related to PAL-1, reader 104 determines that any additional PALs include AIDs to be processed. If all the remaining PALs do not have any AIDs, then method 200 continues to block 214. If another PAL (e.g., PAL-2) includes a preferred AID, then reader 104 may buffer the AID obtained for PAL-1 and may send a SELECT command with the AID residing in PAL-2 to mobile wireless device 102. Mobile wireless device 102 may then determine whether a transaction application 120 identified by the AID residing in PAL-2 is contained in device 102 (e.g., in memory 118). If a transaction application associated with the PAL-2 AID is identified, then mobile wireless device 102 provides application data associated with the transaction application to reader 104.

In block 214, the reader bundles the application data and forwards to a POS terminal. In one embodiment, reader 104 bundles all of the received application data associated with each of identified transaction applications in to a payload. Reader 104 may then be configured to forward the payload to POS terminal 106. Notably, the POS terminal 106 may be able to process and apply both sets application data to the transaction simultaneously. Thus, separate NFC taps for the first set of application data (e.g., payment card application data) and the second set of application data (e.g., loyalty card application data) is not required. In this scenario, as single NFC tap by the mobile device to the reader is all that is required to conduct a payment transaction involving the two sets of application data, i.e., payment card application data and loyalty card data.

Figure 3:
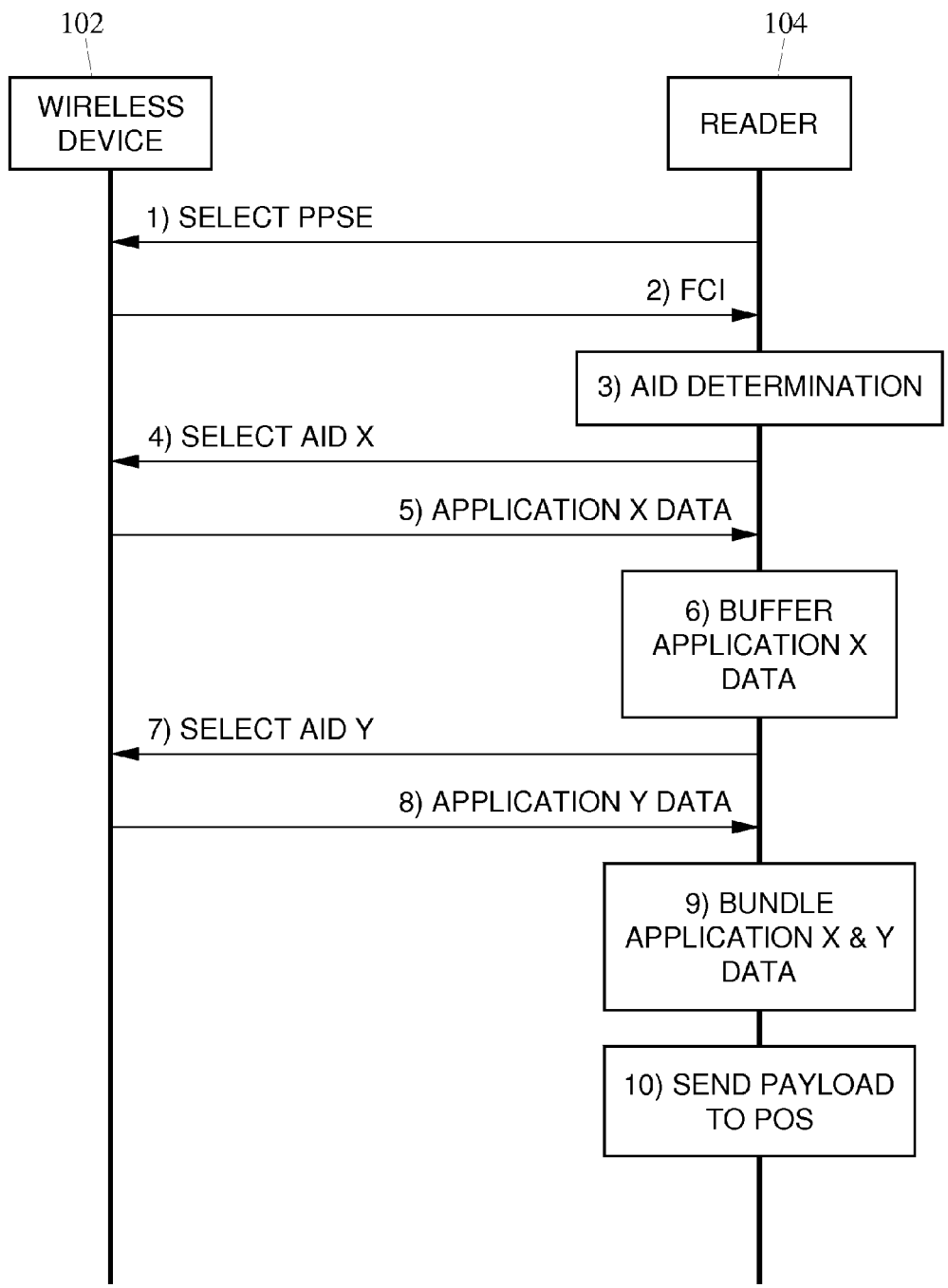
FIG. 3 is a message flow diagram illustrating an exemplary embodiment of messaging between a wireless device and a wireless device reader for utilizing one or more preferred application lists in a NFC reader according to an embodiment of the subject matter described herein.

FIG. 3 is a messaging diagram illustrating an exemplary process for utilizing one or more preferred application lists in an NFC reader as described herein. FIG. 3 illustrates messaging commenced during interfacing wireless device 102 with wireless device reader 104 through a single NFC tap. Prior to step 1, one or more transaction applications may have been previously selected by a user of wireless device 102 such that AIDs associated with the one or more selected transaction applications thereby reside in PPSE application 108. In one embodiment, stored AIDs 110 residing in PPSE application 108 are pre-programmed or pre-selected by a user and are listed in a manner that indicates an order of preference priority. For example, each AID 110 may be respectively associated with a priority level indicator, which may be used to rank each AID 110 in the PPSE 108. In one embodiment, a user of wireless device 102 may have identified and selected any and all transaction applications which can be used to perform a wireless transaction along with his/her order preference as to which application should be used to conduct the wireless transaction. Wireless device 102 may then store the corresponding AIDs 110 in PPSE application 108. In one embodiment, the user can select one or more transaction applications through a communications interface for communicating with a graphic user interface (GUI) or other user interface (UI) on the wireless device. Upon selection, for example, using a touch screen or keypad of wireless device 102, a user may select applications which cause the corresponding AIDs associated with the selected applications to be stored in PPSE application 108. AIDs 110 may be stored within PPSE application 108 using firmware residing on wireless device 102 such that upon interfacing wireless device 102 with wireless device reader 104, the AIDs are provided as an AIDs listing. The AIDs listing may be provided to reader 104 as a PPSE list image, an FCI, and the like. In one example, wireless device 102 may display a list of applications stored in the device 102 using a display screen (not shown). The list may include applications for completing various payment or non-payment transactions. The user can also select the preference in which payment applications are to be used for completing a given payment transaction, for example, attempt to use a VISA® card, a Mastercard card, and a Macy's card (e.g., by ranking or assigning priority indicators to each payment card). AIDs associated with each of the respective payment transaction applications can then be selected and stored in PPSE application 108 according to the priority in which the given AID was selected/designated.

In step 1 of FIG. 3, wireless device 102 NFC taps wireless device reader 104 to initiate a wireless transaction. In responds, reader 104 transmits a "SELECT PPSE" message to request access to PPSE application 108 and the user preferred AIDs 110 stored within. As used herein, user preferred AIDs includes AIDS in which have been ranked in order of preference and/or assigned priority indicators by a user. The "SELECT PPSE" command may include a default command recognized by wireless device 102. Upon receipt of the "SELECT PPSE" command, at step 2, wireless device 102 may send, to reader 104, a PPSE listing that includes user preferred AIDs of all the applications supported by device 102. In one embodiment, the listing indicates to reader 104 the type of applications supported by device 102 as well as each application's designated priority. In one embodiment, the listing includes file command information (FCI) data.

In step 3 of the messaging flow diagram of FIG. 3, reader 104 determines which user preferred AIDs from the received PPSE listing are to be ultimately applied to the wireless transaction. In one embodiment, reader 104 may use ADM 109 to cross-reference the received user preferred AIDs 110 with the preferred AIDs 114 (i.e., compatible) residing in PAL-1 112 in an attempt to find a matching AIDs pair. In one embodiment, PAL-1 112 may include a listing of preferred AIDs 114 that are related with electronic payment cards (e.g., a VISA softcard, Mastercard softcard, Macy's softcard, etc.) that are compatible and supported by the reader and/or transaction terminal 106. Notably, the listing of preferred AIDs PAL-1 112 may indicate the priority and preference of electronic payment cards that the reader 104 is to apply to the wireless transaction. For example, reader 104 may access and check the first preferred AID on PAL-1 112 and determines if a matching entry is found in the PPSE listing of user preferred AIDS received from device 102. If a matching entry is found anywhere within the PPSE listing (regardless of the user priority designation within the PPSE listing), then that single matched AID is identified and the corresponding payment application residing in device 102 may be accessed to provide application data associated with the selected transaction application.

In step 4, after the PAL-1 AID determination process is conducted by reader 104, reader 104 sends an application data request message (e.g., a SELECT message that includes the identified single matched AID (i.e., AID "X") to wireless device 102. In one embodiment, the application data request message includes, for example, a payment card AID selected by reader 104 that is to be used in the wireless transaction. Notably, the SELECT command message is requests application data from the transaction application that corresponds to the selected single matched AID. Although FIG. 3 depicts the use of ANSI protocol (e.g., use of SELECT messages) to request application data, any other protocol may be used without departing from the scope of the present matter.

In step 5, wireless device 102 sends the requested application data to reader 104. In one embodiment, wireless device 102 receives the single matched AID, accesses the transaction application (i.e., application "X") in memory 118 that corresponds to the single matched AID, and obtains the related application data (e.g., payment card account number). The application data (i.e., application "X" data) is then sent from device 102 to reader 104.

In step 6, the received application data is buffered at reader 104. Upon receiving the application data, reader 104 makes a determination as to whether any of the remaining PALs 112 contains a preferred AID. If not then reader 104 forwards the application data to a POS terminal for processing the wireless transaction. If at least one preferred AID is stored in any of the remaining PALs $112_{2...N}$, then reader 104 temporarily buffers the transaction application data for later use and proceeds to step 7.

In step 7, reader 104 issues a separate SELECT command for each preferred AID contained in each PAL. For example, suppose PAL-2 contained an AID corresponding to a specific loyalty card. Reader 104 may access the preferred AID in PAL-2 112$_2$ and issue a SELECT message containing the preferred loyalty card AID (i.e., AID "Y") to wireless device 102.

In step 8, wireless device 102 receives the loyalty card AID, accesses the transaction application (i.e., application "Y") in memory 118 that corresponds to the loyalty card AID, and obtains the related application data (e.g., loyalty card account number). The application data (i.e., application "Y" data) is then sent from device 102 to reader 104. Thus, the user of wireless device 102 phone does not have to manually select a loyalty card while paying with the wireless device 102. Rather, reader 104 sitting at the merchant location will utilize PAL-2 to pull the merchant loyalty card data automatically immediately after receiving the payment card application data during the same NFC tap. The same process described in steps 7 and 8 may be conducted using PAL-3 112$_3$ for an electronic coupon AID or using PAL-N for any other electronic certificate AID that can be applied to the wireless transaction.

In step 9, the application data corresponding to the selected applications (e.g., payment card application X data and loyalty card application Y data) are bundled together into a single payload.

In step 10, the bundled payload is sent to POS terminal 106 for processing. In one embodiment, POS terminal 106 uses the two sets of application data bundled in the single payload to conduct the wireless transaction. More specifically, separate NFC taps for the first set of application data (e.g., payment card application data) and the second set of application data (e.g., loyalty card application data) is not required. In this scenario, as single NFC tap by the mobile device to the reader is all that is required to conduct a payment transaction involving the two sets of application data, i.e., payment card application data and loyalty card data.

In one embodiment, rather than fetching application identifiers residing in the secure element, the wireless reader may also be configured to circumvent the secure element and fetch applications directly from baseband memory. In such a case, the PPSE selected application list the reader obtains from wireless device's secure element may not apply here. Namely, the reader may be configured to request a list of applications from a software program running in the wireless device's baseband memory and be able to select the desired application from the list the reader obtains from baseband memory software program.

In one embodiment, the present subject matter may be utilized with MIFARE applications. Notably, the MIFARE protocol is not AID-driven. A PAL, in order to support MIFARE over ISO14443-4, may specify a special AID, such as "MIFARE-1" or "4D69666172652D31". If the reader finds the MIFARE AID as the first priority in the PAL, the reader does not initiate the PPSE selection process (e.g., no SELECT message is sent). Instead, the reader initiates a MIFARE authentication process. If the authentication process fails, the MIFARE AID is temporarily removed from the PAL list (i.e., only for the present MIFARE card) and the PPSE and PAL matching process (as described above) occurs.

It will be understood that various details of the subject matter described herein may be changed without departing from the scope of the subject matter described herein. Furthermore, the foregoing description is for the purpose of illustration only, and not for the purpose of limitation.

What is claimed is:

1. A system for utilizing one or more preferred application lists (PALs) in a wireless device reader, comprising:
   a transaction terminal configured to designate a plurality of compatible application identifiers, wherein each of the compatible application identifiers is respectively associated with a transaction application that is compatible with the transaction terminal;
   a mobile wireless device provisioned with a proximity payment system environment (PPSE) application that is configured to store a plurality of user preferred application identifiers, wherein each user preferred application identifier is respectively associated with a transaction application stored on the mobile wireless device; and
   a wireless device reader configured to:
   receive the plurality of compatible application identifiers from the transaction terminal,
   store the compatible application identifiers among a plurality of preferred applications lists (PALs) which includes a first PAL containing a first group of the compatible application identifiers, wherein each of the compatible application identifiers in the first group is assigned a priority indicator,
   receive a PPSE list containing the user preferred application identifiers from the PPSE application in response to a wireless transaction initiated by a single near field communication (NFC) tap between the mobile wireless device and the wireless device reader, wherein the user preferred application identifiers are communicated from the mobile wireless device to the wireless device reader in response to the single NFC tap,
   determine one or more matched application identifiers by comparing each of the compatible application identifiers contained in the first PAL with each of the received user preferred application identifiers,
   identify a single matched application identifier from the one or more matched application identifiers, wherein the single matched application identifier corresponds to the user preferred application identifier that matches the compatible application identifier with the highest priority indicator contained in the first PAL, and
   request transaction application data from the transaction application, stored on the mobile wireless device, corresponding to the user preferred application identifier associated with the single matched application identifier.

2. The system of claim 1 wherein the plurality of preferred application lists includes a second PAL containing a second group of the compatible application identifiers.

3. The system of claim 2 wherein the wireless device reader is configured to send a request message for transaction application data from a transaction application associated with a user preferred application identifier that matches a compatible application identifier belonging to the second group.

4. The system of claim 3 wherein the wireless device reader is configured to bundle both the transaction application data associated with the single matched application identifier and the transaction application data associated with the user preferred application identifier that matches the compatible application identifier belonging to the second group in a payload.

5. The system of claim 4 wherein the wireless device reader is configured to send the payload to the transaction terminal to process the wireless transaction.

6. The system of claim 1 wherein the first PAL is designated for listing compatible electronic payment card application identifiers and the second PAL is designated for listing compatible electronic loyalty card application identifiers.

7. The system of claim 6 wherein the plurality of preferred application lists includes a third PAL that is designated for listing at least one of: compatible electronic coupon application identifiers, compatible electronic transit card application identifiers, and compatible electronic healthcare card application identifiers.

8. The system of claim 1 wherein the mobile wireless device includes at least one of: a near field communication (NFC) card, an NFC enabled mobile wireless device, an NFC enabled tablet, and a contactless smart card.

9. The system of claim 1 wherein the wireless transaction includes a near field communication (NFC) transaction.

10. The system of claim 1 wherein the wireless device reader is further configured to request the PPSE list upon initiation of the wireless transaction.

11. The system of claim 1 wherein the PPSE list includes at least one of: an image of user preferred application identifiers stored in the PPSE application and FCI data.

12. The system of claim 1 wherein the transaction terminal includes a point of sale (POS) terminal.

13. A method for utilizing one or more preferred application lists in an NFC reader, the method comprising:
   receiving, by a wireless device reader from a transaction terminal, a plurality of compatible application identifiers, wherein each of the compatible application identifiers is respectively associated with a transaction application that is compatible with the transaction terminal;
   storing, by the wireless device reader, the compatible application identifiers among a plurality of preferred applications lists (PALs) which includes a first PAL containing a first group of the compatible application identifiers, wherein each of the compatible application identifiers in the first group is assigned a priority indicator;
   receiving, by the wireless device reader from a mobile wireless device via a wireless transaction initiated by a single near field communication (NFC) tap between the mobile wireless device and the wireless device reader, a plurality of user preferred application identifiers, wherein each user preferred application identifier is respectively associated with a transaction application stored on the mobile wireless device, wherein the plurality of user preferred application identifiers are communicated from the mobile wireless device to the wireless device reader in response to the single NFC tap;
   determining, by the wireless device reader, one or more matched application identifiers by comparing each of the compatible application identifiers contained in the first PAL with each of the received user preferred application identifiers;
   identifying, by the wireless device reader, a single matched application identifier from the one or more matched application identifiers, wherein the single matched application identifier corresponds to the user preferred application identifier that matches the compatible application identifier with the highest priority indicator contained in the first PAL; and
   requesting, by the wireless device reader, transaction application data from the transaction application stored on the mobile wireless device corresponding to the user preferred application identifier associated with the single matched application identifier.

14. The method of claim 13 wherein the plurality of preferred application lists includes a second PAL containing a second group of the compatible application identifiers.

15. The method of claim 14 comprising sending a request message for transaction application data from a transaction application associated with a user preferred application identifier that matches a compatible application identifier belonging to the second group.

16. The method of claim 15 comprising bundling both the transaction application data associated with the single matched application identifier and the transaction application data associated with the user preferred application identifier that matches the compatible application identifier belonging to the second group in a payload.

17. The method of claim 16 comprising sending the payload to the transaction terminal to process the wireless transaction.

18. The method of claim 14 wherein the first PAL is designated for listing compatible electronic payment card application identifiers and the second PAL is designated for listing compatible electronic loyalty card application identifiers.

19. The method of claim 18 wherein the plurality of PALs includes a third PAL that is designated for listing at least one of: compatible electronic coupon application identifiers, compatible electronic transit card application identifiers, and compatible electronic healthcare card application identifiers.

20. The method of claim 13 wherein the mobile wireless device includes at least one of: a near field communication (NFC) card, an NFC enabled mobile wireless device, an NFC enabled tablet, and a contactless smart card.

21. The method of claim 13 wherein the wireless transaction includes a near field communication (NFC) transaction.

22. The method of claim 13 further comprising requesting a proximity payment system environment (PPSE) list containing the plurality of user preferred application identifiers upon initiation of the wireless transaction.

23. The method of claim 22 wherein the PPSE list includes at least one of: an image of user preferred application identifiers contained in the PPSE list and file control information (FCI) data.

24. The method of claim 13 wherein the transaction terminal includes a point of sale (POS) terminal.

25. A system for requesting transaction application data, the system comprising:
   a transaction terminal configured for designating a plurality of compatible application identifiers respectively associated with a plurality of transaction applications compatible with the transaction terminal;
   a mobile wireless device configured for storing a plurality of user preferred transaction application identifiers, wherein each user preferred transaction application identifier is respectively associated with a transaction application stored on the mobile wireless device; and
   a wireless device reader configured to:
   store the plurality of compatible application identifiers received from the transaction terminal, wherein each of the compatible application identifiers includes a priority indicator,
   receive the plurality of user preferred transaction application identifiers in response to a wireless transaction initiated by a single near field communication (NFC) tap between the mobile wireless device and the wireless device reader, wherein the user preferred transaction application identifiers are communicated from the mobile wireless device to the wireless device reader in response to the single NFC tap,
   determine one or more matched application identifiers by comparing each of the compatible application identifiers with each of the received user preferred transaction application identifiers,
   identify a single matched application identifier from the one or more matched application identifiers, wherein the single matched application identifier corresponds to the user preferred transaction application identifier that matches the compatible application identifier with the highest priority indicator, and
   request transaction application data from the transaction application stored on the mobile wireless device, corresponding to the user preferred transaction application identifier associated with the single matched application identifier.

26. The system of claim 25, wherein the mobile wireless device includes at least one of: a near field communication (NFC) card, an NFC enabled mobile wireless device, an NFC enabled tablet, and a contactless smart card.

27. The system of claim 25 wherein the wireless transaction includes a near field communication (NFC) transaction.

28. The system of claim 25 wherein the wireless device reader is further configured to request a proximity payment system environment (PPSE) list containing the plurality of user preferred transaction application identifiers upon initiation of the wireless transaction.

29. The system of claim 28 wherein the plurality of user preferred transaction application identifiers are received as either an image of user preferred transaction application identifiers contained in the PPSE list or as file control information (FCI) data.

30. The system of claim 25 wherein the transaction terminal includes a point of sale (POS) terminal.

31. A method for requesting transaction application data, the method comprising:
   receiving, by a wireless device reader from a transaction terminal, a plurality of compatible application identifiers respectively associated with a plurality of transaction applications compatible with the transaction terminal, wherein each of the compatible application identifiers includes a priority indicator;
   receiving, by the wireless device reader from a mobile wireless device via a wireless transaction initiated by a single near field communication (NFC) tap between the mobile wireless device and the wireless device reader, a plurality of user preferred transaction application identifiers, wherein each user preferred transaction application identifier is respectively associated with a transaction application stored on the mobile wireless device, wherein the plurality of user preferred transaction application identifiers is communicated from the mobile wireless device to the wireless device reader in response to the single NFC tap;
   determining, by the wireless device reader, one or more matched application identifiers by comparing each of the compatible application identifiers with each of the received user preferred transaction application identifiers;
   identifying, by the wireless device reader, a single matched application identifier from the one or more matched application identifiers, wherein the single matched application identifier corresponds to the user preferred transaction application identifier that matches the compatible application identifier with the highest priority indicator; and
   requesting, by the wireless device reader from the mobile wireless device, transaction application data from the transaction application stored on the mobile wireless device corresponding to the user preferred transaction application identifier associated with the single matched application identifier.

32. The method of claim 31 wherein the mobile wireless device includes at least one of: a near field communication (NFC) card, an NFC enabled mobile wireless device, an NFC enabled tablet, and a contactless smart card.

33. The method of claim 31 wherein the wireless transaction includes a near field communication (NFC) transaction.

34. The method of claim 31 further comprising requesting the plurality of user preferred transaction application identifiers upon initiation of the wireless transaction.

35. The method of claim 31 wherein the plurality of user preferred transaction application identifiers is received as either an image of user preferred transaction application identifiers contained in a proximity payment system environment (PPSE) list or as file control information (FCI) data.

36. The method of claim 31 wherein the transaction terminal includes a point of sale (POS) terminal.

37. A non-transitory computer readable medium having stored thereon computer executable instructions that when executed by a processor of a wireless device reader controls the wireless device reader to perform steps comprising:

receiving, from a transaction terminal, a plurality of compatible application identifiers respectively associated with a plurality of transaction applications compatible with the transaction terminal, wherein each of the compatible application identifiers includes a priority indicator;

receiving, from a mobile wireless device via a wireless transaction initiated by a single near field communication (NFC) tap between the mobile wireless device and the wireless device reader, a plurality of user preferred transaction application identifiers, wherein each user preferred transaction application identifier is respectively associated with a transaction application stored on the mobile wireless device, wherein the plurality of user preferred transaction application identifiers is communicated from the mobile wireless device to the wireless device reader in response to the single NFC tap;

determining one or more matched application identifiers by comparing each of the compatible application identifiers with each of the received user preferred transaction application identifiers;

identifying a single matched application identifier from the one or more matched application identifiers, wherein the single matched application identifier corresponds to the user preferred transaction application identifier that matches the compatible application identifier with the highest priority indicator; and requesting, from the mobile wireless device, transaction application data from the transaction application stored on the mobile wireless device, corresponding to the user preferred transaction application identifier associated with the single matched application identifier.

\* \* \* \* \*